United States Patent [19]

Salanitro

[11] Patent Number: 5,750,364
[45] Date of Patent: May 12, 1998

[54] BIODEGRADATION OF ETHERS USING AN ISOLATED MIXED BACTERIAL CULTURE

[75] Inventor: Joseph Patrick Salanitro, Houston, Tex.

[73] Assignee: Shell Oil Company, Houston, Tex.

[21] Appl. No.: 465,996

[22] Filed: Jun. 6, 1995

[51] Int. Cl.$^6$ ............................ C12P 39/00; C12S 00/00
[52] U.S. Cl. ........................ 435/42; 435/262; 435/262.5; 435/821
[58] Field of Search ................... 435/42, 252.1, 435/262, 262.5, 821; 210/601, 610, 611, 612, 613, 620, 626

[56] References Cited

U.S. PATENT DOCUMENTS

| | | | |
|---|---|---|---|
| 4,009,099 | 2/1977 | Jeris | 210/612 |
| 4,391,887 | 7/1983 | Baumgarten et al. | 435/42 |
| 4,415,454 | 11/1983 | Fuchs | 210/616 |
| 5,474,934 | 12/1995 | Adamus et al. | 435/262.5 |
| 5,536,410 | 7/1996 | Kitatsuji et al. | 210/626 |

OTHER PUBLICATIONS

J. Salanitro et al., "Isolation of Bacterial Culture That Degrades Methyl t–Butyl Ether", *Applied and Environmental Microbiology*, Jul. 1994, pp. 2593–2596.

K. Mo et al., "Biodegradation of Methyl t–Butyl Ether by Pure Bacterial Cultures", *Applied Microbiol Biotechnol*, 1997, pp. 69–72.

R. Cowan et al., "Biodegradation of the Gasoline Oxygenates MTBE, ETBE, TAME, TBA, and TAA by Aerobic Mixed Cultures", *Hazardous and Industrial Wastes Proceedings of the Twenty–Eighth Mid–Atlantic Industrial and Hazardous Waste Conference*, Jul. 1996, pp. 523–531.

H. M. Jensen et al., "Solubility and Degradability of the Gasoline Additive MTBE, methyl–tert–butyl–ether, and Gasoline Compounds in Water", *Contaminated Soil '90*, pp. 445–448.

J. M. Suflita et al., "Anaerobic Biodegradation of Known and Potential Gasoline Oxygenates in the Terrestrial Subsurface", *Environ. Sci. Technol.*, 1993, pp. 976–978.

P. Pitter et al., "III. Aliphatic Alcohols, Thiols, Aldehydes, Ketones, Ethers, and Acids and Their Derivatives", *Biodegradability of Organic Substances in the Aquatic Environment*, 1990, pp. 179–190.

Y. Fujiwara et al., "Biodegradation and Bioconcentration of Alkyl Ethers", *Yukagaku 33* (No. 2), 1984, pp. 111–115.

M. R. Mormile et al., Anaerobic Biodegradation of Gasoline Oxygenates: Extrapolation of Information to Multiple Sites and Redox Conditions, *Environmental Science & Tech.*, vol. 28, 1994, pp. 1727–1732.

Ann–Soffie Allard et al., "The Aerobic Biodegradation of Tert–Butyl Methyl Ether and Tert–Butanol: An Initiatory Study", *IVL Report B1197, Institute for Vatten och Luftvardsforskning*, Mar. 1996, pp. 1–8.

Fujiwara et al., "Biodegradation and Bioconcentration of Alkyl Ethers", Yukagaku 33:111–114 (1984).

Moller et al., Solubility and Degradability of the Gasoline Additive MTBE . . . Contaminated Soil (1990), 445–448, Kluwer Academic Publishers.

Suflita, J.M. & M. R. Mormile, Anaerobic Biodegradation of Known and Potential Gasoline Oxygenates in the Terrestrial Subsurface, Environ. Sci. Tech. 27:976–978 (1993).

Parales et al., *Degradation of 1,4–dioxane by an Actinomycete in Pure Culture*, Applied Environ. Microbiol., 60, 4527–4530, May 1994.

ATCC Catalogue of Bacteria and Bacteriophage 18th ed., 1992, p. 372.

Pelczar et al. Microbiology, 4th ed., 1977, p. 215 and pp. 795–803.

Brock. Biology of Microorganisms, 3rd ed. 1979 pp. 353–355.

*Primary Examiner*—Leon B. Lankford, Jr.
*Assistant Examiner*—Christopher R. Tate
*Attorney, Agent, or Firm*—Y. Grace Tsang

[57] ABSTRACT

An isolated mixed bacterial culture, preferably BC-1, ATCC No. 202057, which degrades ethers, especially branched alkylethers including MTBE, under aerobic conditions has been prepared.

9 Claims, 1 Drawing Sheet

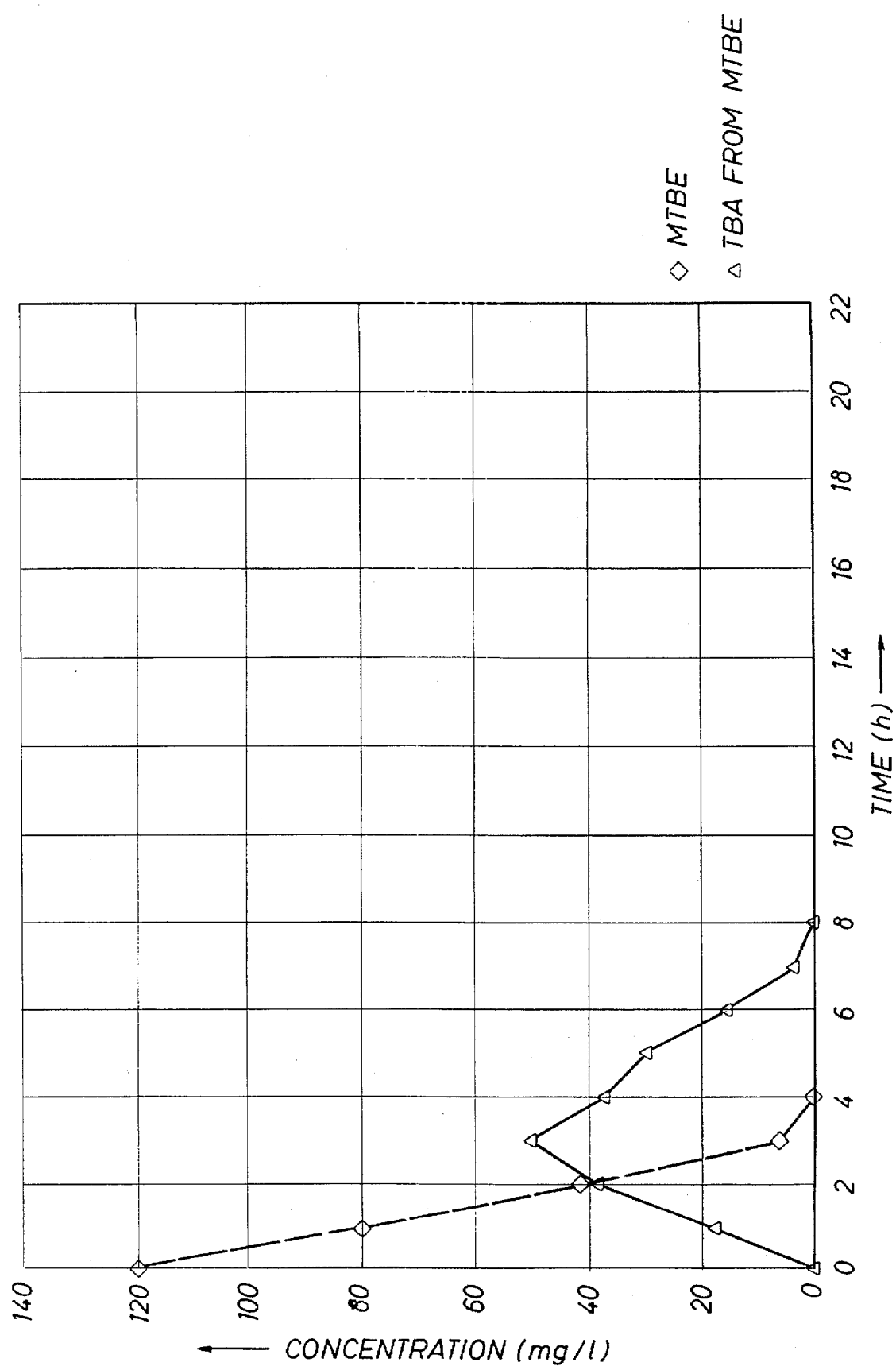

BIODEGRADATION OF ETHERS USING AN ISOLATED MIXED BACTERIAL CULTURE

FIELD OF THE INVENTION

This invention relates to a process for degrading ethers, such as methyl t-butyl ether (MTBE), utilizing a bacterial culture developed from microorganisms present in a chemical plant biotreater sludge. This invention further relates to a bacterial culture capable of degrading ethers, including methyl t-butyl ether (MTBE), and the process for preparing such culture.

BACKGROUND OF THE INVENTION

Alkyl-alkyl ethers (R-O-R) such as methyl t-butyl ether (hereinafter "MTBE") are being used as octane-enhancers in the reformulation of low volatility unleaded gasoline blends and for reducing the emission of volatile organic compounds from engines. In general, alkylethers, especially those alkylethers which have only one ether linkage and without other functional groups, are chemically stable compounds and there is little information on their biodegradability in soil, groundwater and activated sludge environments. The lack of alkylether degradation by indigenous microbes in soils and biosludges may be attributed to the very stable and chemically unreactive ether linkage, the inability of these compounds to be transported into cells and/or the lack of inducible or existing enzyme activities (e.g. oxygenases, hydroxylases) which can attack the ether bond.

It is known that MTBE can persist in groundwater from accidental spills of unleaded gasoline from underground storage tanks. However, no known naturally-occurring microbial cultures exist to biotreat groundwater, wastewater, tank bottom wastes or soils containing this ether.

Alkyl ethers such as symmetric dioctyl ether have been shown by Modrzakowski and Finnerty to be only partially oxidized by an Acinetobacter strain in which the ether linkage is not cleaved and only the terminal carbons are utilized for growth. See Intermediary Metabolism of Acinetobacter Grown on Dialkyethers. Can J. Microbiol., 35:1031–1036 (1989).

Studies on the biodegradability testing of MTBE in sludges and soils by Fujiwara et al. showed that 100 ppm MTBE or diisopropylether (DIPE) does not degrade in activated sludge (300 ppm solids) in an oxygen uptake assay. Moreover, MTBE did not significantly affect the respiration rate of other hydrocarbons when blended (12% w/v) with the fuel. See Fujiwara, T., T. Kinoshita, H. Sato and I. Kojima, Biodegradation and bioconcentration of alkyl ethers. Yukagaku 33: 111–114 (1984).

Moller and Arvin proposed that MTBE (10 ppm) or TAME (t-amyl methyl ether, 3 ppm) were not degraded in 60 days by microbes in an aquifer soil, topsoil or activated sludges. In these experiments, MTBE at 200 ppm levels showed a weak inhibitory effect on the biodegradation of aromatic hydrocarbons (3.5 ppm BTEX). See Moller, H. and E. Arvin, Solubility and Degradability of the Gasoline Additive MTBE, methyl-tert-butyl-ether and Gasoline Compounds in Water, Contaminated Soil '90, 445–448 (1990), Kluwer Academic Publishers.

Recent studies by Suflita and Mormile on the anaerobic degradation of gasoline oxygenates in a landfill aquifer material showed that of several alkyl ethers tested (MTBE, TAME, ETBE, DIPE, ethyl ether, propyl ether) only n-butyl methyl ether was metabolized under anaerobic methanogenic conditions. MTBE is only cleaved under anaerobic condition to t-butyl alcohol which is not degraded further. See Suflita, J. M. and M. R. Mormile, Anaerobic Biodegradation of Known and Potential Gasoline Oxygenates in the Terrestrial Subsurface. Environ. Sci. Technol. 27: 976–978 (1993).

Parales et al isolated actinomycete from biosludge which was shown to grow on 1,4-dioxane could also utilize some of the linear alkyl ethers such as diethyl ether and methyl butyl ether, but not the branched alky ethers such as diisopropylether, ethyl t-butyl ether or ethylene glycol ethers. See Parales, R. E., J. E. Admus, N. White, H. D. *Degradation of 1,4-dioxane by an Actinomycete in Pure Culture*, Applied Environ Microbial, 60, 4527–4530, May, 1994.

Japanese patent application number 04,110,098, filed by Kyowa Hakko Kagyo KK, proposes the decomposition of ethyleneglycol alkylethers with bacteria. The ethers decomposed have more than one ether linkages and/or have hydroxyl functional groups, which are known to be more readily degradable than those with only one ether linkage and without other functional groups.

Japanese patent application number 62,208,289, filed by Hodogaya Chem Ind KK, proposes the degradation of polyoxytetramethylene glycol with bacterial strains. The ethers degraded have multiple ether linkages and thus are more readily degradable than those with only one ether linkage and with no other functional groups.

Thus, there remains a need for a bacterial culture capable of degrading under aerobic condition an ether, especially an alkyl ether, more especially a branched alkyl ether such as MTBE. The culture would be useful for treating wastes and groundwater containing ethers, especially branched alkyl ethers such as MTBE.

SUMMARY OF THE INVENTION

This invention relates to (a) a bacterial culture capable of degrading alkylethers, especially branched alkylethers including MTBE, under aerobic conditions; (b) a process for preparing a bacterial culture which is capable of degrading alkylethers, especially branched alkylethers such as MTBE, to $CO_2$ using activated sludges; (c) a process for the aerobic degradation of ethers, especially branched alkylethers such as MTBE, using a mixed bacterial culture (BC-1) prepared from activated sludges; (d) a process for remediating wastes and groundwater containing ethers, especially branched alkylethers such as MTBE, to reduce the alkylether(s) content thereof by growing in the presence of said wastes and groundwater a population of a mixed bacterial culture (BC-1) prepared from activated sludges.

BRIEF DESCRIPTION OF THE DRAWING

The drawing illustrates a non-limiting example of a culture of the present invention, which degrades a solution containing 120 mg/L of MTBE to close to 0 mg/L of MTBE in about 4 hours. The TBA, as an intermediate, is degraded to close to 0 mg/L in about 8 hours.

DETAILED DESCRIPTION OF THE INVENTION

A culture of BC-1 has been deposited with the American Type Culture Collection (ATCC), Patent Depository, 12301 Parklawn Drive, Rockville, MD. 20852 with ATCC number 202057. A culture of BC-1, ATCC number 202057, can be obtained from the permanent collection of the ATCC, Patent Depository.

The present invention involves a novel mixed bacterial culture capable of degrading a branched alkyl ether. Particularly, the present invention involves a novel mixed bacterial culture capable of degrading aerobically a branched alkyl ether to $CO_2$. The mixed bacterial culture is capable of cleaving the ether linkage of methyl t-butyl ether (MTBE) with the transient formation of t-butyl alcohol (TBA) and degrading completely to $CO_2$. The novel mixed bacterial culture can also metabolize other linear and branched ethers. Non-limiting and illustrative examples of the linear and branched ethers include diethyl ether (DEE), dimethyl ether (DME), methyl ethyl ether (MEE), methyl n-propyl ether (MPE), ethyl n-propyl ether, methyl isopropyl ether, ethyl isopropyl ether, diisopropyl ether (DIPE), ethyl t-butyl ether (ETBE) or methyl-t-amyl ether. Specifically, the invention relates to a novel mixed bacterial culture, designated BC-1 with ATCC No. 20257, which is capable of degrading MTBE completely to $CO_2$ with the transient formation of t-butyl alcohol (TBA).

As a more specific embodiment of the present invention, the novel mixed bacterial culture includes any composition derived from the mixed bacterial culture enriched from incubating activated sludge and a branched alkyl ether. Illustrative examples of the compositions derived from the mixed bacterial culture include, but not limited to, fragments of bacterial culture, membrane fragments of bacterial culture, enzymes extracted and/or isolated from the bacterial culture, lyophilized and/or dried culture, lyophilized and/or dried fragments of culture, lyophilized and/or dried enzymes derived from said culture, bacterial culture and/or fragments thereof and/or enzymes derived therefrom bound to a carrier and/or binder and/or fixed bed, etc. Any method known to one skilled in art for making composition derived from the mixed culture including but not limited to extraction or fragmentation to obtain active ingredients/fragments thereof is within the scope of the present invention. As one non-limiting example of the present invention, the mixed culture can be first fragmented by sonification or lysing with lysozyme and/or a compound such as a chelating compound, followed by salting out the enzyme fractions using ammonium sulfate or NaCl.

The present invention also relates to a process for preparing the above-mentioned novel mixed bacterial culture by adding a branched alkyl ether such as MTBE to an activated sludge obtained from a biotreater located in a wastewater treatment plant. As a specific embodiment of the present invention, the activated sludge is retrieved from the biotreater located in a wastewater treatment plant of a chemical plant. As a still more specific embodiment of the present invention, the activated sludge is retrieved from the biotreater of the South Effluent Treater for treating wastewater from the Chemical Plant of Shell Deer Park Manufacturing Complex located at 5900 Highway 225, Deer Park Tex. 77536.

The culture is prepared by adding a branched alkyl ether to the biosludge (activated sludge) and incubating for a period time. As one specific embodiment of the present invention, the biosludge is first added to a mineral nutrient solution. One specific, but non-limiting, example of the mineral solution is Sturm solution comprising $KH_2PO_4$, $K_2HPO_4$, $Na_2HPO_4 \cdot 2H_2O$, $MgSO_4 \cdot 7H_2O$, $NH_4Cl$, $(NH_4)_2SO_4$, and $FeCl_3 \cdot 2H_2O$. Incubation using other nutrient solution known to those skilled in the art is within the scope of the present invention. The concentration of the biosludge in the incubated medium (culture) can be any suitable amount which would produce sufficient concentration of ether degrading bacteria. In a specific embodiment of the present invention, from about 50 mg to about 5000 mg, more specifically from about 50 mg to about 1500 mg, still more specifically from about 300 to about 800 mg, of the biosludge solids are added to every liter of the incubation medium.

The above culture is enriched by adding a suitable amount of branched alkyl ether. In a specific embodiment of the present invention, about 5–5000 mg, more specifically about 10–500 mg, still more specifically about 30–50 mg, of the branched alkyl ether is added to every liter of the culture (incubation medium or mixture).

The mixture or culture is incubated for a period of time. The typical temperature at which the culture is incubated ranges from about 5° C. to about 80° C., specifically from 10° C. to about 60° C., more specifically from about 15° C. to about 35° C., still more specifically from about 22° C. to about 25° C. Periodically, a sample of the culture (or supernatant) is withdrawn for branched alkyl ether analysis. A culture is active in degrading branched alkyl ether if there is detectable reduction of the concentration of the branched alkyl ether in the culture being enriched, after taken into account of the amount of branched alkyl ether evaporated. As an illustrative but non-limiting example, a culture which is considered very active in degrading branched alkyl ether will degrade a solution containing about 0.001–5000 ppm, more specifically about 0.01–500 ppm, still more specifically about 0.05–100 ppm, of branched alkyl ether by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours. As an illustrative non-limiting example, a culture is capable of degrading a solution containing 120 mg/L of MTBE to close to 0 mg/L of MTBE in about 4 hours.

In one specific embodiment of the present invention, the mixture of the activated sludge and the mineral solution is first flushed with oxygen before the addition of the branched alkyl ether.

In still another specific embodiment of the present invention, periodically, a portion in an amount of about 5–80%, specifically about 10–70%, more specifically about 40–60%, of the supernatant of the culture is withdrawn and fresh mineral or nutrient solution is added to at least partially replace the amount of supernatant withdrawn. The withdrawal can be conducted at an interval of about 1–30 days, specifically 2–10 day, more specifically about 5–8 days.

As another specific embodiment of the present invention, multiple additions of branched alkyl ether are subsequently made to the culture (incubating medium) after the first addition of the branched alkyl ether. The subsequent additions were made at least two days after the first addition of the branched alkyl ether. As a specific aspect of this embodiment, sufficient amount of branched alkyl ether is added either immediately after each withdrawal of the supernatant or simultaneously with the addition of the replacement portion of mineral or nutrient solution, thereby compensating the loss of the branched alkyl ether resulted from the withdrawal. As another specific aspect of this embodiment, sufficient alkyl ether is added each time designed to maintain the alkyl ether concentration at about 50–150%, specifically about 80–120%, of the original concentration.

As a preferred embodiment of the present invention, multiple additions (re-inoculation) of the activated sludge is made to the culture periodically, such as at an interval of about 2–60 days, specifically about 3–30 days, more specifically about 5–10 days. In a specific aspect of this embodiment, from about 50 mg to about 5000 mg, more specifically from about 50 mg to about 1500 mg, still more specifically from about 300 to about 800 mg, of biosludge solids are added to every liter of the incubation medium at each re-inoculation.

Illustrative examples of the branched alkyl ether suitable for the enrichment of the culture to produce the culture of the present invention include, but not limited to, MTBE, diisopropyl ether, ethyl t-butyl ether, di-t-butyl ether, diisobutyl ether, isopropyl isobutyl ether, isopropyl t-butyl ether, isopropyl isobutyl ether, t-amyl methyl ether, t-amyl ethyl ether, t-amyl propyl ether, t-amyl isopropyl ether, t-amyl n-butyl ether, t-amyl isobutyl ether, t-amyl methyl ether, etc.

As a preferred embodiment of the present invention, methyl t-butyl ether (MTBE) is used in the enrichment of the bacterial culture to produce a MTBE degradable culture.

The enrichment process typically lasts from about 1 months to about one year, more typically from about 1.5 months to 5 months, more typically from about 2 months to about 4 months.

As a more preferred embodiment of the present invention, the culture produced is capable of degrading alkyl ethers, specifically branched alkyl ethers, more specifically MTBE, to carbon dioxide. The culture prepared can also be used to degrade t-butyl alcohol, isopropyl alcohol and acetone.

The present invention further involves a process for degrading ethers, including alkylethers and aromatic ethers utilizing the above-mentioned novel culture by contacting or growing the aforementioned culture or composition derived from the culture with or in a solution containing the ether to be degraded. The alkylethers include branched alkyl ether and linear alkyl ethers. Specifically, the process of the present invention is effective in degrading branched alkyl ether, particularly MTBE. As a specific embodiment of the present invention, the ether to be degraded can be an ingredient in an aqueous solution such as groundwater and wastewater, a solid mixture such as soil, etc. The degradation is preferably conducted under an oxygen-containing atmosphere, such as aerobic conditions. The degradation can be conducted at a temperature from about 5° C. to about 80° C., specifically from about 10° C. to about 60° C., more specifically from about 15° C. to about 35° C., still more specifically at ambient temperature.

As a specific embodiment of the present process, the bacterial culture is used to remediate groundwater and wastewater containing ether, specifically alkyl ether, more specifically MTBE.

It is known that when MTBE-containing fuels are accidentally released to the subsurface, this alkyl ether is the most water soluble and persistent compound in ground water. Other branched alkyl ethers which behave similarly and have also been considered by the oil industry as octane enhancers for motor fuels are diisopropyl ether (DIPE), ethyl tertiary butyl ether (ETBE) and methyl tertiary amyl ether (MTAE). The present invention thus provides an effective biological process for remediating these ethers accidentally released to the subsurface such as groundwater, wastewater and soil. In a specific embodiment of the present invention, the ethers can be completely mineralized to carbon dioxide by a suitable culture prepared by the aforementioned enrichment process. Hence, the remediation process can be substantially free of environmentally undesirable end products.

The present process is capable of degrading/-remediating ether(s), specifically branched alkyl ether(s), more specifically MTBE, in an aqueous mixture containing from about 0.001 ppm to about 5000 ppm, specifically from about 0.01 ppm to about 500 ppm, more specifically from about 0.05 ppm to about 100 ppm of the ether(s); to reduce the content thereof by from about 10% to about 100%, specifically from about 30% to about 100%, more specifically from about 50% to about 100%, still more specifically from about 80% to about 100% in from about 2 hours to about 70 hours, specifically from about 2 hours to about 12 hours, more specifically from about 3 hours to about 5 hours, by growing in the aqueous mixture the culture of the present invention.

As a specific embodiment of the present invention, the isolated bacterial enrichment culture can cleave the ether linkage of MTBE with the transient formation of t-butylalcohol (TBA). The t-butylalcohol can be degraded by the culture to carbon dioxide. It can also metabolize other linear and branched ethers including diethyl ether (DEE), dimethyl ether (DME), methyl ethyl ether (MEE), methyl n-propyl ether (MPE), ethyl n-propyl ether, methyl isopropyl ether, ethyl isopropyl ether, diisopropyl ether (DIPE), ethyl t-butyl ether (ETBE) or methyl-t-amyl ether (MTAE), etc.

The invention will be illustrated by the following illustrative embodiments which are provided for illustration purpose only and are not intended to limit the scope of the instant invention.

ILLUSTRATIVE EMBODIMENTS

The following illustrative embodiments describe typical techniques of the present invention.

Part A: Derivation of Ether Degradable Culture
A-I: BC-1 Ether Degradable Culture Derived From Activated Sludge from Chemical Plant Biotreater The biosludge (activated sludge) used in this run (A-I) was retrieved from the biotreater of the South Effluent Treater for treating wastewater from the Chemical Plant of Shell Deer Park Manufacturing Complex located at 5900 Highway 225, Deer Park Tex. 77536. About 100–200 ml of the biosludge (activated sludge) containing about 300 to 800 mg of biosludge solids were added to 1 liter of Sturm solution containing the following minerals (in milligrams per liter, i.e. ppm) to form a culture in a 2-liter stirred glass vessel sealed with Viton O rings: $KH_2PO_4$, 17; $K_2HPO_4$, 44; $Na_2HPO_4 \cdot 2H_2O$, 67; $MgSO_4 \cdot 7H_2O$, 23; $NH_4Cl$, 3.4; $(NH_4)_2SO_4$, 40; $FeCl_3 \cdot 6H_2O$, 1. Information on this mineral solution can be found in Sturm, R. N., Biodegradability of nonionic surfactants: screening test for predicting rate and ultimate degradation. J. Am. Oil Chem. Soc. 50: 159–167 (1973).

The above culture was enriched by first flushing with oxygen for 5 minutes, followed by adding MTBE at an amount of about 30–50 mg MTBE per liter of the culture.

The culture was stirred continuously at room temperature (22°–25° C.). At weekly intervals, 1–3 ml of the slurries were withdrawn and allowed to settle (or be filtered). The supernatant and samples (1–3 ml supernatant) withdrawn for MTBE analysis. At each sampling, the culture was enriched by removing 500 ml of supernatant medium and replacing with 500 ml of the sterile minerals solution containing 30–50 ppm MTBE. No significant reduction of MTBE concentration in the supernatants sampled was detected for about two months.

Starting two months after the commencement of the enrichment procedure, re-inoculation involving multiple additions of about 100–200 ml of the above-described activated-sludge retrieved from Shell Deer Park Chemical Plant biotreater was made to the culture about every 7–30 days for about two months. The above-mentioned enrichment procedure of periodic additions of MTBE and withdrawal of the supernatant was also continued.

After two months, this enriched culture became active in consistently degrading MTBE concentrations in the supernatant about 50% to about 100% in about 2–4 hours. This culture was subsequently designated BC-1.

A-II: Control-1% NaCN

A vessel used as a control was prepared following the enrichment procedure described in A-I above using the same biosludge material, except sufficient NaCN was added so that the culture contains 1% NaCN. NaCN was used as a microbial respiration inhibitor to monitor any ether loss from volatilization.

Results:

The Control (A-II) showed less than 10% loss of ether from volatilization. Mixed culture made from A-I, subsequently designated BC-1, ATCC No. 202057, consistently degraded MTBE.

Microscopic and Species Characteristics of BC-1 Culture

Microscopic examination of phase-contrast and gram-stained smears of BC-1 showed that it contains gram-positive filamentous species and several gram-negative smaller rod-shaped bacteria. Preliminary identification of colonies isolated on a minerals (Sturm solution) agar medium containing 200 ppm of MTBE indicate that BC-1 contains at least 4–5 organisms including species of coryneforms, Pseudomonas and Achromobacter. All of these isolates utilize acetate, but none have been shown to grow on MTBE as sole source of carbon.

Part B: Maintenance and Anaysis of BC-1 in a Bench Biotreater

The BC-1 culture obtained from A-I above was placed into a four-liter capacity sealed glass vessel for continuous culture maintenance. A similar suspended solids recycle apparatus with aerator (4L) and clarifier (1L) has been described in Salanitro et al, *Effects of Ammonia and Phosphate Limitation on the Activated Sludge Treatment of Calcium-Containing Waste*, Biotechnol. Bioeng. 25 513–523 (1983), with the exception that pure oxygen was used in place of air to provide aerobic conditions. Dissolved oxygen was monitored with a Leeds and Northrup 7932 meter and probe and maintained at 4–7 mg/liter (ppm) with an oxygen flow rate of 10 ml/min. MTBE (2% solution) was added continuously at a rate of 30–40 ml/day (150–200 mg/liter (ppm)) using a Watson-Marlow (Model 101U) peristaltic pump. The pH was kept at 7.2–7.5 by the infusion of 2 M NaOH solution from a Masterflex® peristaltic pump. The culture was also fed with a minerals solution (4 liters/day) consisting of NaCl (1,000 ppm), $NH_4CL$ (380 ppm), $KH_2PO_4$ (350 mg/liter (ppm)), and $MgSO_4 \cdot 7H_2O$ (30 ppm). The ether-degrading culture developed a stable nitrifying population under high $NH_4^+$ (380 mg/liter (ppm) $NH_4Cl$) or low $NH_4^+$ (65 mg/liter (ppm) $NH_4Cl$) conditions. Suspended solids removed from the unit included 35–40 ml/day from the aerator (intentionally wasted) and 8 to 48 mg/day from the effluent. This waste rate was equivalent to a 80–90 day cell residence time.

Influent and effluent samples from the continuous biotreater were analyzed for cell dry weight according to methods outlined in Standard Methods for the examination of water and wastewater, 17th ed. Method 5210-B, American Public Health Association, Washington, D.C. $NH_4^+$, $NO_3^-$ and $PO_4^{-3}$ ions were estimated by routine Dionex® ion chromatography.

Data on the growth and metabolism of the BC-1 culture in the solids recycle culture are given in TABLE 1 below.

TABLE 1

Nitrification and Biomass Yields in BC-1 Continuous Culture Degrading MTBE

| Parameter[a] | Nitrifying Condition | |
|---|---|---|
| | High $NH_4^+$ | Low $NH_4^+$ |
| Influent $NH_4^+$, ppm | 120–125 | 10–20 |
| Effluent $NO_3^-$, ppm | 390–450 | 50–70 |
| Reactor TSS, ppm[b] | 2500–2580 | 2020–2340 |
| Solids retention, days | 80–90 | 80–85 |
| Average % MTBE removed | 80–90[c] | 60–65[d] |
| Cell yield, g TSS/g MTBE utilized | 0.21–.24 | 0.23–.28 |

[a] Analyses given are the average of four weeks data under each condition.
[b] Waste rates were 1.1–1.31 every four weeks; effluent TSS under both conditions varied from 2–12 ppm and contributed 25–30% of biomass loss from the unit.
[c] Influent and effluent MTBE varied from 160–210 ppm and 3–40 ppm, respectively.
[d] Influent and effluent MTBE varied from 120–175 ppm and 50–60 ppm, respectively.

Part C: Batch Substrate Removal Experiments

The utilization of MTBE and t-butyl alcohol (TBA), a possible major metabolite of MTBE, was assessed in batch removal assays with BC-1. In this test, individual compounds were added (120–130 ppm) to one liter of BC-1 culture in a 1.5 liter vessel. Before addition of each compound, the culture was flushed with sterile 100% $O_2$ in a 1.5 liter sealed vessel for 2–5 minutes to achieve a dissolved oxygen level of 20 ppm. The reaction vessel was stirred continuously at 22°–25° C. and the depletion of substrates monitored by sampling (2–3 ml) over a 24 hours period. MTBE and TBA were analyzed by methods described below.

Analysis of MTBE and TBA

Culture samples were analyzed for MTBE and t-butanol using a Hewlett-Packard Model 280 gas chromatography-flame ionization detection system. Compounds were separated on a Quadrex methyl silicone (1-μm-thick film) capillary column having dimensions 25 m long and 0.025 mm inside diameter. (Alltech/Applied Science Labs, State College, Pa.). The column was set initially at 30° C. for 3 minutes and then programmed to 70° C. at 20° C./min. The carrier gas consisted of helium (30 ml/min) and a $N_2$ make-up gas. One microliter split samples were analyzed. Retention times of TBA and MTBE were 3 and 3.8 min, respectively.

Results of Substrate Removal Experiments

Results of batch substrate depletion assays with BC-1 in the presence of MTBE are shown in FIG. 1. MTBE (120 mg/liter) was rapidly degraded, within 4 hours at a rate of 34 mg/g of cells per hour. TBA was formed as a transient metabolic product of MTBE breakdown. The highest levels of TBA were reached after MTBE was completely utilized. TBA formed from MTBE declined at a slower rate (14 mg/g of cells per hour) than did MTBE. These results provide evidence that BC-1 degrades MTBE to TBA as a primary intermediate.

Part D: Oxygen Update Experiments

Oxygen uptake rates (OUR) were performed on the BC-1 culture in the presence of substrates and potential metabolic intermediates of MTBE. A Yellow Springs Instrument Company oxygen electrode-water bath assembly (Model 53; 5 ml reaction compartment) was used for these experiments. Suspended solids (TSS) from BC-1 were centrifuged (23,900×g, 10 min at 4° C.), resuspended to one-half the volume in a sterile phosphate-buffered saline solution, PBS (0.85% NaCl, 0.03M $Na_2HPO_4$ and 0.05M $KH_2PO_4$, PH7.2). The 2X concentrated culture was aerated (sterile house air) continuously at 30° C. and maintained at a dissolved oxygen level of 6–7 ppm before using in OUR experiments. About 0.01–0.03 g TSS were used in each reaction. Substrates were added at levels of 15 or 50 ppm from sterile stock (1,000 ppm) solutions and oxygen depletion monitored over 3–5 minutes at 30° C. The oxygen electrode and the dissolved oxygen concentration was interfaced and calibrated to the deflection of a 1 mV recorder (Houston Instrument Company) and rates calculated from the slopes of the tracings. OUR are given as mg oxygen utilized/g TSS/h.

The ability of BC-1 to oxidize MTBE and potential downstream degradation products and other cellular intermediates was determined by oxygen uptake rate (OUR) methods and these data are shown in Table 2. Highest OUR was observed with $NH_4^+$, however, allylthiourea, a specific inhibitor of $NH_4+$ oxidation, completely blocked this oxygen utilization. MTBE showed two distinct OUR, an initial faster (5.2–5.9 mg $O_2$/g/hr) and a slower (50% less) rate. Addition of allylthiourea had no effect on oxygen utilization in the presence of MTBE. t-Butylformate (TBF, t-butyl-COOH), an intermediate in the reaction of atmospheric-derived chloride and hydroxy free radicals with MTBE also enhanced oxygen uptake in BC-1. t-Butanol, isopropanol and lactate showed comparable OUR to MTBE (4.3–7 mg/g/h).

TABLE 2

Oxygen Uptake Rates (OUR) with Culture BC-1[a]

| Substrate[b] | Net OUR mgO$_2$/g TSS/h |
|---|---|
| 1. $NH_4^+$ | 17.4 |
| 2. $NH_4^+$ + allylthiourea | —[c] |
| 3. Allylthiourea | —[c] |
| 4. MTBE | 5.2–5.9, 2.3[d] |
| 5. MTBE + allythiourea | 5.2 |
| 6. t-Butylformate (Na) | 7.2 |
| 7. t-Butanol | 6.0 |
| 8. Isopropanol | 4.3 |
| 9. Lactate (Na) | 7.0 |

[a]Continuous culture treating high NH4+ (120 ppm) and MTBE (150–200 ppm) levels.
[b]All compounds added at 50 ppm.
[c]Less than or equal to the endogenous OUR.
[d]First and second OUR.

Part E: Radiolabled MTBE Experiments

The $^{14}CH_3O$-MTBE was custom synthesized by Amersham Corp., (Arlington Heights, Ill.). It had a specific activity of 1.19μ Ci/mg and was 99.3% pure by radiochromatography. Cultures were centrifuged, washed and resuspended in the same volume of sterile PBS buffer (PBS, 0.85% NaCl, 0.03 M $Na_2HPO_4$, 0.05M $KH_2PO_4$, pH 7.2), and placed in 125 ml serum bottles sealed with Teflon® lined septa. $^{14}CH_3O$-MTBE was added to a concentration of 0.08μ Ci/ml and MTBE at 2 ppm. Cultures were incubated at 30° on a rotary shaker (150–200 rpm) for seven days. The amount of $^{14}CO_2$, formed was determined by placing a 10-ml aliquot of the culture in a similar serum bottle, adjusting the pH to ≦2 with 6N HCl and then flushing the bottle for one hour with a steady stream of $N_2$ into three gas washing bottles containing 0.1M Ba $(OH)_2$. The $Ba^{14}CO_3$ precipitate (formed after co-precipitation with $Na_2CO_3$ addition) was collected onto 0.45 μm Millipore filters, washed with PBS, dried and the radioactivity was counted. After removal of $^{14}Co_2$, the culture was filtered onto a 0.22 μm Millipore filter, washed with PBS, dried and counted to estimate $^{14}C$ activity incorporated into biomass (cells). The remaining radioactivity in the filtrate represents undegraded $^{14}CH_3O$-MTBE and/or $^{14}C$-metabolites. The efficiency of trapping $^{14}CO_2$ by this method was confirmed in separate experiments in which $NaH^{14}CO_3$ was added (0.06 μCi, 70 ppm as $CO_2$) to PBS or azide-inhibited cultures, acidified (pH ≦2) and flushed into $Ba(OH)_2$ traps as described. The recovery of $H^{14}CO_3^-$ as $Ba^{14}CO_3$ was 95–100% of the applied radioactivity. The $^{14}C$-radioactivity was determined by placing 1-ml amounts of culture fluid (total $^{14}C$) filtrates or filters containing $Ba^{14}CO_3$ precipitates into glass scintillation vials containing 15 ml Aquasol-2 Universal 2SC Cocktail (NEN Dupont Research Products, Boston, Mass.). Vials were counted in a Packard TRI-CARB (Model 2500 TR) liquid scintillation analyzer (Packard Instrument Co., Meriden, Conn.).

Results of the biodegradation of radiolabeled ether (2 ppm) by BC-1 are given in Table 3. Less than 1% and 5% of the applied isotope was recovered as $^{14}CO_2$ and $^{14}C$-cells, respectively, in the abiotic (no culture) control and cultures containing the respiration inhibitor, sodium azide (2%). About 80% of the 14CH$_3$O-MTBE was incorporated into $CO_2$ and cells with the remainder (ca. 15%) as undegraded ether and/or $^{14}C$-metabolites. Addition of 100 ppm $NH_4^+$ to metabolizing cultures had no competitive effect on stimulating or inhibiting MTBE biotransformation.

TABLE 3

Distribution of $^{14}CH_3O$-MTBE in Ether-Degrading Cultures

| | % of Applied $^{14}CH_3O$-MTBE[a] in | | | |
|---|---|---|---|---|
| Condition | CO$_2$ | Cells | MTBE &/or Metabolites | % Recovery |
| 1. Control (no cells) | 0.2 | 4.1 | 13.7 | 18 |
| 2. BC-1[b] + Azide (2%) | 0.9 | 5.1 | 17.1 | 23.1 |
| 3. BC-1 | 39.0 | 42.1 | 17.8 | 98.9 |
| 4. BC-1 + NH$_4^+$ (100 ppm) | 42.3 | 40.3 | 12.5 | 95.1 |

[a]Mean of duplicate cultures did not differ by more than 10%.
[b]Suspended solids as TSS and VSS were 2440 and 1820 ppm, respectively.

CHEMICALS

Common laboratory chemicals e.g. salts, bases acids, alcohols and ketones used were purchased from Mallinckrodt or Sigma Chemical Companies. MTBE and TBA were obtained as ≧98% pure material from Chem Service Inc. of West Chester, Pa.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

What is claimed is:

1. An isolated mixed bacterial culture having all the identifying characteristics of BC-1, ATCC No. 202057.

2. An isolated mixed bacterial culture having the identifying characteristics of BC-1, ATCC No. 202057, wherein said culture degrades methyl-tert-butyl ether (MTBE) to carbon dioxide within 70 hours.

3. An isolated mixed bacterial culture culture having the identifying characteristics of BC-1, ATCC No. 202057, wherein said culture aerobically degrades at least 10% of MTBE, added to the culture at a concentration of 0.01 to 500 ppm, within 70 hours.

4. The mixed bacterial culture of claim 3, which culture also degrades t-butyl alcohol.

5. An isolated mixed bacterial culture culture having the identifying characteristics of BC-1, ATCC No. 202057, wherein said culture aerobically degrades at least 10% of MTBE, added to the culture at a concentration of 0.01 to 500 ppm, to carbon dioxide within 70 hours.

6. An isolated mixed bacterial culture culture having the identifying characteristics of BC-1, ATCC No. 202057, which culture degrades to carbon dioxide MTBE and one or more of the following ether compounds: diisopropyl ether, ethyl-t-butyl ether, di-t-butyl ether, disobutyl ether, isopropyl isobutyl ether, isopropyl t-butyl ether, t-amyl methyl ether, t-amyl ethyl ether, t-amyl propyl ether, t-amylisopropyl ether, t-amyl-n-butyl ether, t-amyl isobutyl ether, and t-amyl methyl ether within 70 hours.

7. The mixed bacterial culture of claim 6, wherein the culture degrades at least 10% of tertiary carbon-containing ether compounds, added to the culture at a concentration of 0.01 to 500 ppm, to carbon dioxide in about 2 to 70 hours.

8. The mixed bacterial culture of claim 6, wherein the culture degrades at least 10% of tertiary carbon-containing ether compounds in about 3 to 5 hours.

9. An isolated mixed bacterial cultureculture having the identifying characteristics of BC-1, ATCC No. 202057, which culture degrades to carbon dioxide MTBE and one or more of the following tertiary carbon-containing ether compounds: ethyl-t-butyl ether, t-amyl-n-butyl ether, t-amylisobutyl ether, isopropyl t-butyl ether, t-amyl ethyl ether, t-amylpropyl ether, t-amylisopropyl ether, and methyl t-amyl ether within 70 hours.

* * * * *